United States Patent [19]

Carson

[11] Patent Number: 4,461,281
[45] Date of Patent: Jul. 24, 1984

[54] ARTHROSCOPIC SURGICAL APPARATUS AND METHOD

[76] Inventor: Robert W. Carson, 1419 Circle Way, Salt Lake City, Utah 84103

[21] Appl. No.: 806,833

[22] Filed: Jun. 15, 1977

[51] Int. Cl.$^3$ .............................................. A61B 17/00
[52] U.S. Cl. ......................................... 128/3; 128/6; 128/303 R; 128/305; 128/343
[58] Field of Search ...................... 128/1 R, 2 B, 3, 4, 128/329 R, 347, 214.4, 303 R, 92 E, 92 R, 92 EB, 343, 6, 305

[56] References Cited

U.S. PATENT DOCUMENTS

| | | | |
|---|---|---|---|
| 3,528,425 | 9/1970 | Banko | 128/329 |
| 3,663,965 | 5/1972 | Lee et al. | 3/1 |
| 3,719,186 | 3/1973 | Merig | 128/92 EB |
| 3,805,770 | 4/1974 | Okada | 128/1 R X |
| 3,830,225 | 8/1974 | Shinnick | 128/2 B |
| 3,856,020 | 12/1974 | Kovac | 128/214.4 X |

OTHER PUBLICATIONS

*Atlas of Arthroscopy*, Chapters IV and X, (1969).

Primary Examiner—Michael H. Thaler
Attorney, Agent, or Firm—Trask & Britt

[57] ABSTRACT

Surgical apparatus includes a first and second inserter each having a handle and a shaft secured to and extending away from the handle. A collar is secured to the distal end of the shafts. The first inserter has an elongated blade secured to and extending away from the collar and the shaft. The second inserter has an elongated blunt member secured to and extending away from the collar and the shaft. The surgical apparatus includes a sleeve member having a head sized to be grasped by the fingers of the user and having a hollow cannula extending away from the head. An aperture is formed in the head to correspond with the channel in the hollow cannula. The blade of the first inserter is positioned through the channel with the head abutting the collar. The blade extends beyond the distal end of the cannula and is inserted through the skin, subcutaneous tissue and fascia of a patient at a preselected location proximate an articulate joint. Thereafter the first inserter is removed while the sleeve is held in place by grasping the head with the fingers. The second inserter is then positioned through the channel with the head abutting the collar and the blunt end extending beyond the distal end of the cannula. Thereafter the second inserter is inserted to penetrate the synovial lining proximate the joint. Then the second inserter is withdrawn leaving the sleeve member in position. Surgical instruments may be inserted through the sleeve members.

6 Claims, 15 Drawing Figures

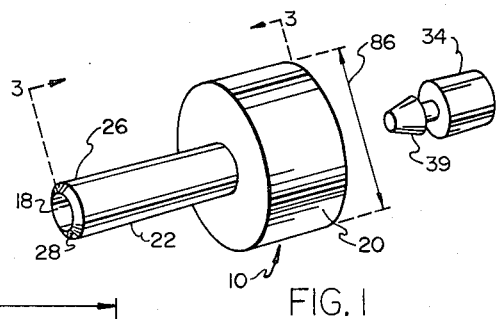
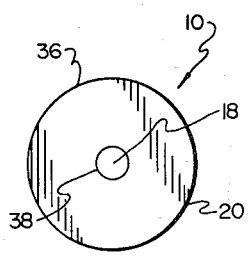
FIG. 1  FIG. 2
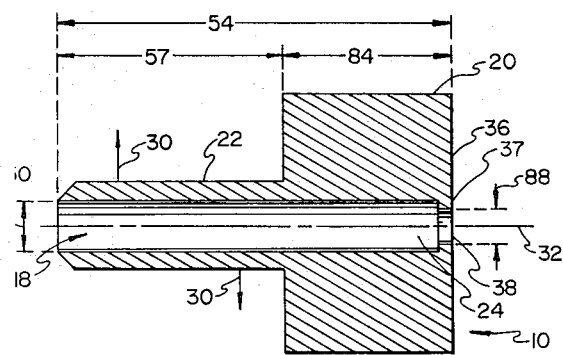
FIG. 3
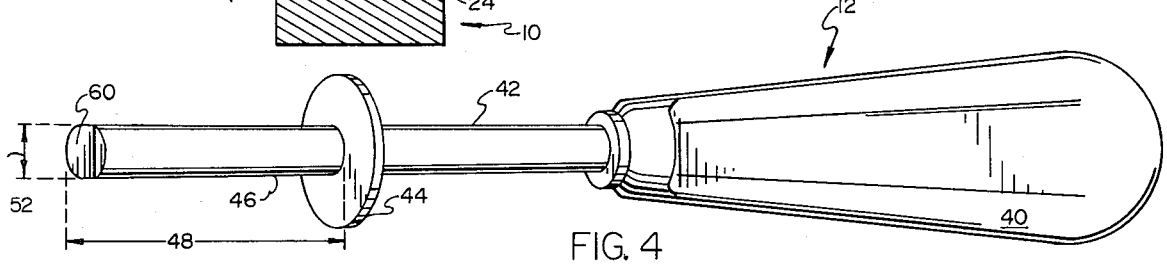
FIG. 4
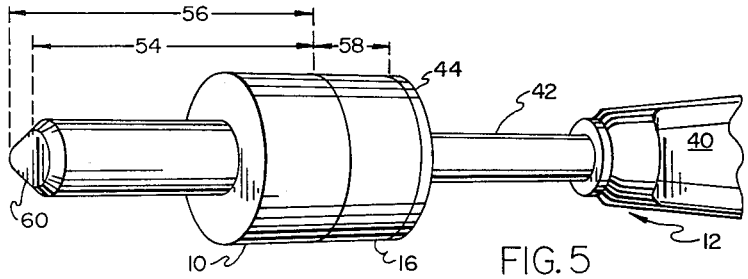
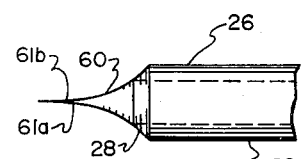
FIG. 5  FIG. 6
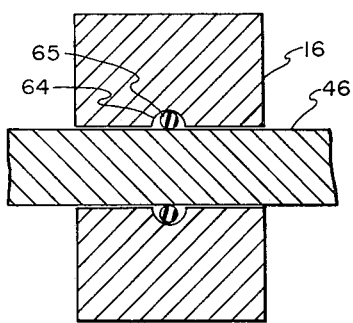
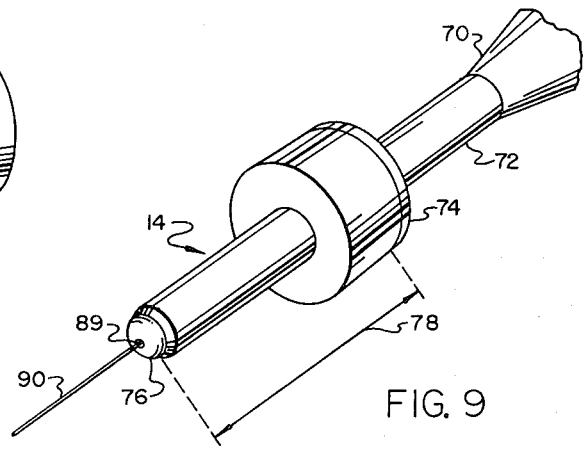
FIG. 8  FIG. 7  FIG. 9

ARTHROSCOPIC SURGICAL APPARATUS AND METHOD

BACKGROUND OF THE INVENTION

1. Field

This invention relates to surgical procedures and apparatus. More particularly, this invention discloses apparatus and procedures for performing therapeutic arthroscopic surgical procedures.

2. State of the Art

Arthroscopic diagnosis using an arthroscope and its associated equipment is well known. M. Watanabe, Takeda and H. Ikeuchi, *Atlas of Arthroscopy* (Igaku Shoin Ltd., Tokyo, Second Ed. 1969). Use of the arthroscope permits a treating physician to actually view the interior of an articulate joint (e.g., knee) for the purpose of diagnosing conditions. Although the arthroscope has facilitated diagnosis, no significant improvement in surgical procedures associated with articulate joint maladies has ensued.

Arthroscopic diagnosis is generally effected through one or two short stab wounds. The stab wounds have been found to heal rather quickly and to cause reduced discomfort and disability for the patient. However, treatment of diagnosed conditions may require surgery. Surgical treatment of an articulate joint is typically effected through long surgical incisions which serverely disables a patient for weeks, even months, as the wound heals.

For example, meniscectomy (cartilage removal) of the knee is a standard, common, well accepted surgical procedure. The conventional technique requires an arthrotomy incision of two to three inches in length through the skin and subcutaneous tissue of the patient proximate his knee. Thereafter the damaged or defected cartilage is removed and the incision closed. Postoperative hemorrhage, inflammation and pain inhibit the quadricep muscle mechanism and prolong disability because of the extended incision. After conventional meniscectomy at least three to four days of hospitalization are required. After hospitalization, at least two weeks of crutch walking and often four or more weeks of lost time from work or other physical activity is experienced by the patient. Rehabilitation during this time is typically supervised by a physical therapist with concomitant cost to the patient.

Partial meniscectomy is now being accomplished by a very small number of Arthroscopists through small stab wound incisions. Partial meniscectomy consists of removing only a small torn part of the meniscus sparing the major attached outer rim. A partial meniscectomy results in less hemorrhage, inflammation and noticeably short disability when performed through stab wounds. A parial meniscectomy is effected using long metal barrels which are 4 to 7.5 millimeters in diameter and very thin straight long handled instruments. The barrels are totally unyielding and severely restrict the use of instruments and in turn the acceptability of the procedure. Indeed, the apparatus and procedures which are known have not been sufficient to permit any significant effect of surgical knee procedures except through extended incisions (e.g., large open wounds).

Other deficiencies or maladies associated with articulate joints are similarly painful and expensive in treatment. Extensive surgical procedures after diagnosis (for example, by arthroscope) consume a significant amount of time for attending surgeons, hospital personnel, and the patient. The associated cost of the procedure is in turn quite significant.

Known instrumentation is not suitable or adapted for use in the vicinity of an articulate joint or to facilitate operative surgical procedures in an articulate joint area. For example, bacterial seals such as that disclosed in U.S. Pat. No. 3,815,577, have been used to create a permanent communication between the interior of the body and the anterior of the body. U.S. Pat. No. 3,663,965 (Lee Jr. et al.) similarly attempts to provide a bacterial resistant device which nonetheless permits communication between the interior and anterior portions of the body. Such devices are made only of solid material and restrict instrument passage and manipulation.

U.S. Pat. No. 3,253,594 (Mathews et al.) discloses a peritoneal cannula. This device is designed to be left in the abdomen or within the peritoneum over a long period of time. Its purpose is to pass fluids in and out of the abdomen for procedures including, for example, peritoneal lavage. The device is designed to prevent infection and to seal and self-retain safely and effectively. It is a rigid metal device with no provision for passing instruments of any kind whatsoever into or out of the peritoneal cavity.

U.S. Pat. No. 3,960,143 (Terada) discloses an Endoscope which is used primarily in the abdomen and the peritoneal cavity and secondarily in the chest area. The device provides for means to conduct biopsies within the respective cavities by use of improvements which limit the amount of discomfort or pain experienced by the patient during the course of the biopsy procedure and subsequent thereto. No provision is made to allow for other surgical instruments to pass therethrough.

Other references which may be of interest include U.S. Pat. No. 3,608,544 (Schnepper); U.S. Pat. No. 3,964,468 (Schulz); U.S. Pat. No. 3,989,033 (Halpern et al.); U.S. Pat. No. 3,173,414 (Guillant). The above-mentioned patents appear to describe apparatus for performing biopsies and related surgical procedures involving the removal of a small sample of tissue for diagnostic purposes.

SUMMARY OF THE INVENTION

Arthroscopic surgical apparatus includes first and second inserters each having a handle and a shaft secured to and extending away from the handle. A collar is secured to the distal end of each of the shafts. The first inserter has an elongated blade secured to and extending away from the collar and the shaft. The second inserter has an elongated blunt member secured to and extending way from the collar of the shaft. The apparatus includes a sleeve which has a head sized to be grasped by the fingers of the user. The head has an aperture formed therethrough and a hollow cannula affixed thereto over the aperture along one surface of the head to extend away from the head. The cannula is sized in axial length to extend from the skin surface through the subcutaneous tissue, the fascia and synovial layer into a joint area. The aperture and the cannula form a continuous channel through the sleeve sized to receive the blade and the blunt member. The cannula and the head are sized in combined axial length less than the length of the blade and less than the length of the blunt member.

Preferably the sleeve includes sealing means to make a seal proximate the anterior opening of the channel in the head. The sealing means may be a removable plug to seal the anterior opening. Most preferably, the sleeve is fabricated from a flexible and distortable material.

In a preferred embodiment, the blade is a sharp planer blade with a rounded tip; and the blunt member has a smoothly shaped tip. The blade and blunt members are substantially the same in axial length and in cross-section, the cross-section being slightly less than the cross-section of the channel to permit easy movement of the blade and blunt members therethrough. The interior end of the cannula is shaped to the contour of the blade.

In another embodiment, the second inserter may have a small channel formed therethrough. The apparatus includes an elongated wire sized in length to be longer than twice the length of the second inserter and sized in cross-section to fit within the channel. In yet another embodiment, a shim abuts the collar; and the head of the sleeve abuts the shim. The shim is sized in cross-section substantially the same as the size of the collar and has an aperture sized to permit the shim to be slidably inserted over the cannula to abut the collar.

In a highly preferred embodiment, the cannula is fabricated from a preselected colored material to be readily discernible when positioned through the synovial lining of an articulate joint by viewing means positioned to view the area within the synovial lining.

The surgical procedure includes positioning a preselected quantity of hollow, flexible sleeves to extend from the anterior surface of the patient through the synovial layer into the articulate joint area. Viewing apparatus, which may preferably be an arthroscope, is positioned through the synovial layer in the vicinity of the sleeve devices. Thereafter surgical instruments are inserted through the hollow sleeve devices and manipulated to effect therapeutic procedures within the joint area while viewing the interior area through the viewing apparatus. The sleeve devices are preferably positioned with a first inserter having a collar which abuts the anterior end of the sleeve and a blade which extends through and beyond the interior end of the sleeve. The first inserter is positioned through the sleeve member and inserted through the skin, subcutaneous tissue and fascia of a patient in the vicinity of an articulate joint. Thereafter the first inserter is removed and a second inserter having a collar which abuts the anterior end of the sleeve and a blunt member which extends through and beyond the interior end of said sleeve is inserted through the sleeve member which is being held in position by the fingers of an operator. The second inserter is then inserted to carry the interior end of the sleeve device through the synovial lining of the articulate joint.

BRIEF DESCRIPTION OF THE DRAWINGS

In the drawings, which best illustrate the best mode presently contemplated for carrying out the invention:

FIG. 1 is an exploded perspective view of a sleeve member of a surgical apparatus of the instant invention;

FIG. 2 is a top view of the sleeve member of FIG. 1;

FIG. 3 is a cross-sectional view of the sleeve of FIG. 1 along the section lines 3—3;

FIG. 4 is a perspective view of a first inserter of the instant invention;

FIG. 5 is a partial perspective view of a first inserter of the instant invention with a sleeve member adapted thereto;

FIG. 6 is a partial top view of the tip area of the first inserter with sleeve of FIG. 5;

FIG. 7 is a perspective view of a shim for use with the first and second inserters of the instant invention;

FIG. 8 is a cross-sectional view of a shim adapted to an inserter;

FIG. 9 is a partial perspective view of a second inserter of the instant invention with a sleeve member adapted thereto;

DESCRIPTION OF THE ILLUSTRATED EMBODIMENT

Figure 10:
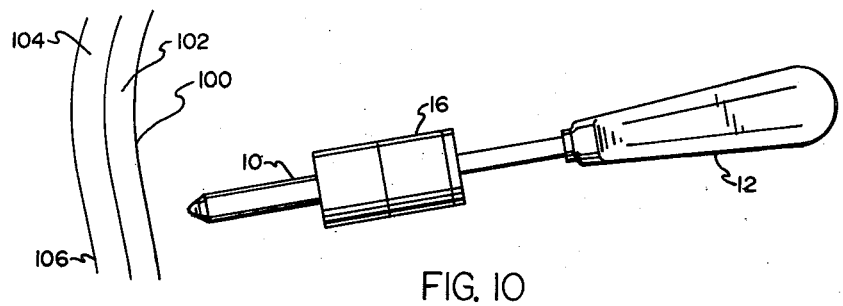
FIGS. 10 through 14 show a first and a second inserter with a sleeve member and shim of the instant invention and several of the steps of their use.
Figure 11:
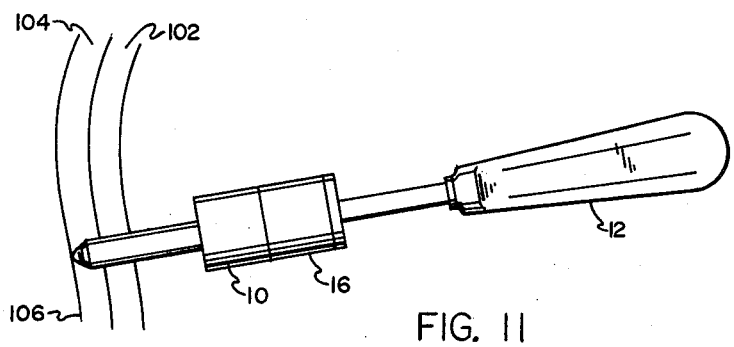
Figure 12:
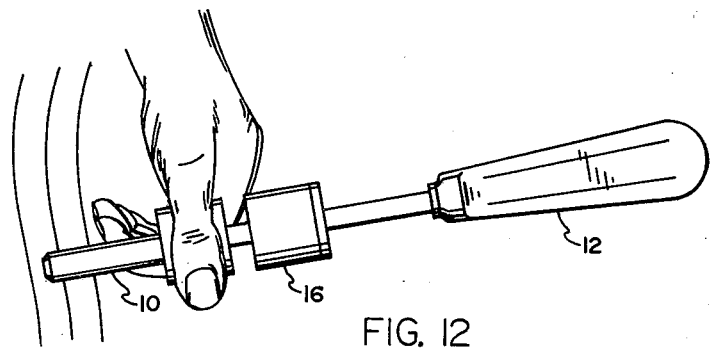
Figure 13:
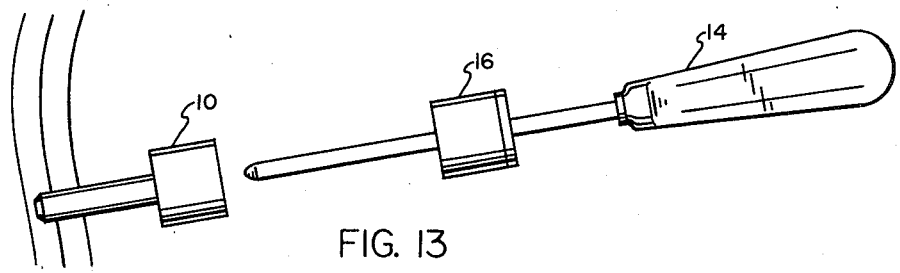
Figure 14:
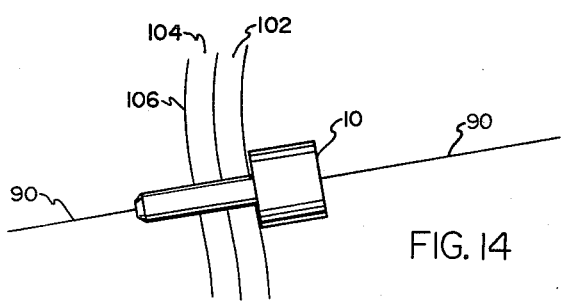

The surgical apparatus of the instant invention includes a sleeve member 10 (FIG. 1), a first inserter 12 (FIG. 4), a second inserter 14 (FIG. 9), and a shim 16 (FIG. 7). The sleeve 10 has a hollow channel 18 formed therethrough. The inserters 12 and 14 are positioned through the channel to insert the sleeve into the body of a patient as more fully discussed hereinafter.

The sleeve 10 has a head 20 and a cannula 22. The cannula 22 is adapted to the head 20 by conventional means including glue or any other means known to those skilled in the art. The channel 18 through the cannula 22 interconnects with a corresponding aperture 24 formed in the head 20 to form the channel 18. The interior or distal end 26 of the cannula 22 has a tip 28 which is angulated or shaped, as hereinafter described, to permit ease of entry through the skin, subcutaneous and fascia of a patient. Preferably, the tip 28 is shaped to provide a smooth relationship between the tip of the first inserter and the tip 28 of the sleeve. The sleeve 10 is preferably constructed from a flexible or distendable material which is generally non-reactive. The material chosen may be medical grade teflon, rubber compound or plastic. A primary consideration is that the material be elastically distendable with the exertion of transverse forces as shown by the arrows 30 in FIG. 3. The material should also have substantial axial 32 strength for ease of insertion.

The sleeve member 10 preferably includes sealing means, which as shown in FIG. 1 is a cap 34 sized to fit within the anterior surface 36 aperture 38 of the channel 18. Other sealing means may be used to seal the aperture 38 as known to those skilled in the art. The lip 37 acts as a retaining surface to retain the plug tip 34 when the plug is inserted and to provide a seal for instruments as more fully discussed hereinafter.

FIG. 4 shows a first inserter having a handle 40 with a shaft 42 secured thereto and extending away therefrom. A collar 44 is adapted to the end of the shaft which extends a preselected distance away from the handle 40. An elongated blade 46 is secured to the collar 44 to extend away therefrom, as here shown, generally in a coaxial manner. The handle 40 is preferably sized to fit comfortably in the palm of the hand of a user. The blade 46 is sized in axial length 48 to penetrate the skin, subcutaneous and fascia of the patient in the vicinity of an articulate joint. As shown in FIG. 5, the blade 46 is sized to fit within the channel 18. That is, the cross-section or diameter 50 of the channel 18 is sized slightly larger than the cross-sectional or diameter 52 of the blade 46. Therefor the blade 46 fits snugly yet slideably and removably within the channel 18 of the sleeve 10.

The sleeve 10 may vary in axial length 54 to accommodate patients of different size. Practically, two sizes should be sufficient, viz: a normal size and a long size. The normal size is for use with most adult patients; and the long size for large or obese patients. The shim 16 is provided to permit use of the two (or more) different size sleeves 10 with the same inserters 12 and 14. As best shown in FIG. 5, the axial length 54 of a normal length sleeve 10, when added to the axial length 58 of the shim 16, is slightly less than the total strength 56 plug 58 from the tip 60 to the collar 44. The long size sleeve (not shown) is sized so that the length 57 of the cannula 22 (FIG. 3) is increased by the length 58 of the shim 16 which is, when the long size is used, removed from inserters 12 and 14.

As here shown, the shim 16 (FIG. 7) may be removably secured to the blade 46 by securing means, which as shown in FIG. 8, is a channel 64 formed in the shim 16 to cooperate with a compressible ring 65 positioned within the channel 64. The ring 65 is slightly smaller in diameter than the diameter of the blade 46 and blunt member 76 so that when the shim 16 is positioned thereover, the ring 65 compresses and frictionally holds the shim 16 in position.

Referring to FIG. 6, it can be seen that the tip 60 of the blade 46 is particularly sharp and arcuate to fair or smoothly associate with the tip 28 of the cannula 22. The shape of the tip 28 is angulated to provide, in effect, a smooth or faired interface between the end or tip of the blade 60 and the cannula 22 ot minimize resistive force as the inserter and sleeve are pushed through the skin and subcutaneuous tissue of a patient. The tip 60 of the blade 46 has been found to be particularly useful when inserted parallel to the fibers of the fascia. The opposite concave surfaces 61a, 61b of the tip 60 part or separate the fibers. Cutting of herniation of the fascia is thus essentially avoided to reduce discomfort and to reduce the extended healing period associated with herniation of the fascia.

Referring now to FIG. 9, the second inserter 14 is shown having a handle 70 with a shaft 72 adapted thereto. A collar 74 is adapted to the shaft 72. A smooth and blunt tipped member 76 is adapted to the collar 74 to extend away therefrom. The collar 74, the shaft 72, the handle 70, and the member 76 are generally assembled to be coaxial. The coaxial length 78 between the tip of the blunt member 76 and collar 74 is selected to be slightly more than the axial length 54 of a long sized sleeve. Alternately, the length may be set for a normal length 54 sleeve 10 by the use of a shim 16 as described with respect to the first inserter 12.

The sleeve member 10 is preferably made of a medical grade silicon colored to be visible through an arthroscope, as hereinafter described. It is possible that a fragment of the sleeve 10 could be inadvertently torn off and float loose within the body of a patient. The coloring would make the fragment distinctive and apparent to the user to facilitate its discovery and removal.

The sleeve 10 should also preferably be sized to be suitable for finger control and manipulation. The head is appropriately sized to facilitate the required finger control capability. As presently envisioned, the head would be approximately 15 mm long 84, and approximately 13 mm in diameter 86. The anterior aperture 38 of the channel 18 at the same time would be about 3 mm in diameter 88. The inner diameter 50 of the channel 18 is preferably about 5 mm. The tip 60 of the blade 46 is sharp and in a single plane as shown by FIG. 6. It has rounded corners to facilitate penetration of the subcutaneous tissue and fascia of the patient as well as the capsule of the knee by dividing the fibers of the fascia rather than cutting across them as do conventional arthroscopic trocars. Use of the single plane blade, as shown in FIGS. 4 and 6, specifically limits a common complaint of arthroscopy. That is, inflamation and pain due to herniation of the fat pad associated with an articulate joint is minimized.

Preferably the axial length 48 and 78 of the blade 46 and blunt member 76 is approximately 40 mm. The shim is selected to be approximately 10 mm thick. The sleeves 10 may be sized in length 54 to be approximately 30 mm for normal and 40 mm for obese (long size) or larger patients. Other lengths 54 may be provided as desired for particular use. It may be noted that the shim 16 and collar 44 and 74 are sized in diameter to be substantially the outside diameter of the head 20 of the sleeve 10.

A second inserter 14 may have a small diameter aperture or hole 89 formed therethrough along its length to receive a thin flexible wire 90 as best shown in FIG. 9. The wire 90 is longer than the length of the inserter 14 and the sleeve 10. It may be inserted through the top of the handle 70 and down the axial length of the second inserter 14 for localization of the stab wound upon removal of the blunt inserter 14 and the sleeve 10. That is, it may be desirable to remove the inserter 14 and/or sleeve and flex the articulate joint. The tissue layers may therefore move to misalign the stab wound tract through the tissue. Without the wire to localize the tract, a new wound may be needed. In other words, use of the wire 90 can reduce the number of stab wounds required. Thewire 90 is preferably stiff.

Referring now to FIGS. 10 through 14, a normal length sleeve member is installed over the blade 46 of a first inserter 12 to abut a shim 16. The blade 46 is positioned proximate the skin 100 of a patient at a site selected by the user. The blade is thereafter inserted through the skin 100, the subcutaneous 102, and fascia 104 of the patient approaching, but not penetrating, the synovial layer 106 using hand pressure. The fingers are then used to grasp the head 20 of the sleeve; and the first inserter is withdrawn. The second inserter 14 with a shim 16 is then positioned down the channel 18 of the sleeve 10. Pressure is then exerted so that the blunt end of the blunt member 76 penetrates the synovial layer 106 proximate the joint area of an articulate joint. The second inserter 14 is then removed while the sleeve member 10 remains in position (FIG. 5). The plug 34 is normally promptly positioned in the anterior aperture 38 of the sleeve 10 to minimize leakage of liquid which is placed in the joint area under pressure.

Figure 15:
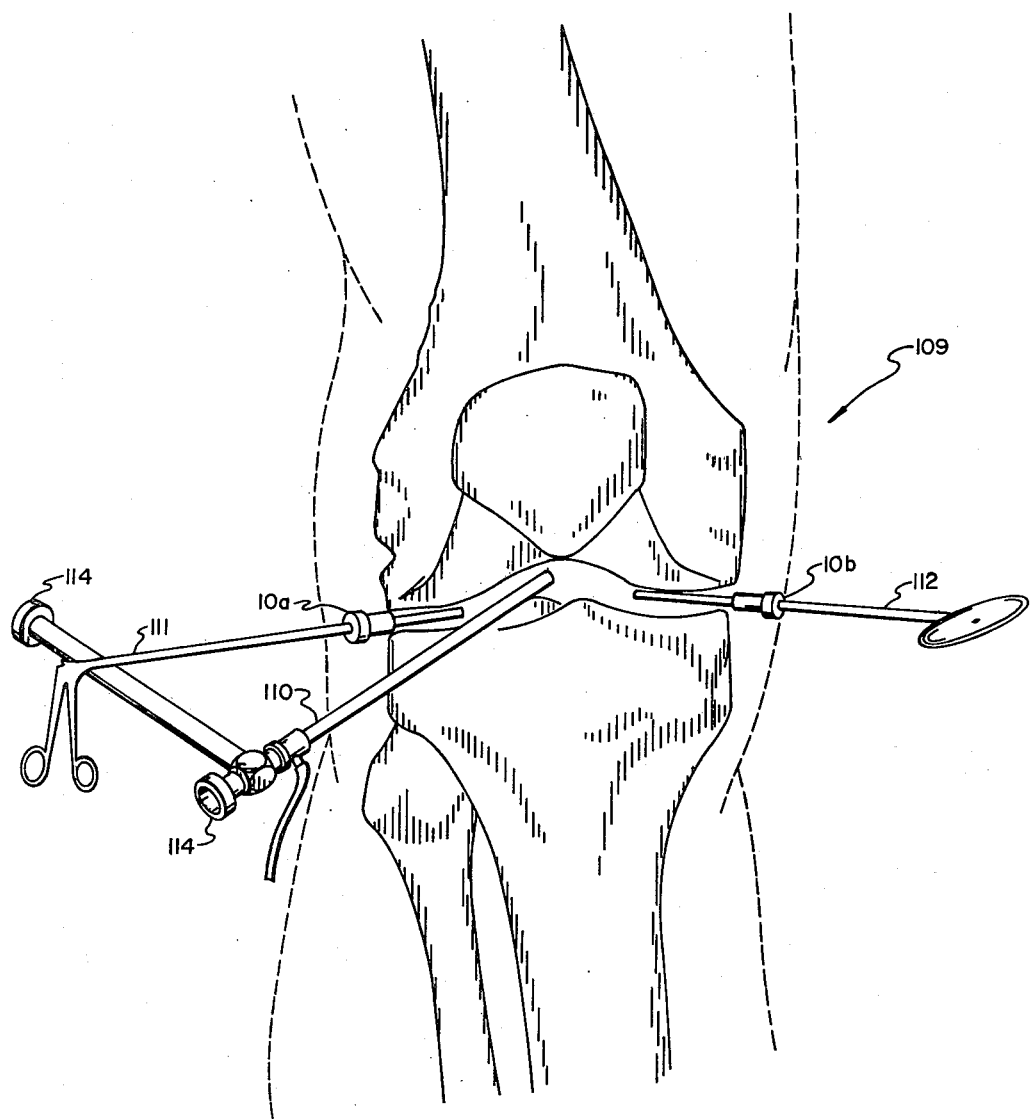
FIG. 15 is a perspective view of an articulate joint of a patient showing apparatus of the instant invention positioned for performing therapeutic and diagnostic procedures.

FIG. 15 shows the knee joint 109 of a patient. An arthroscope 110 is shown in a lateral inferior insertion through the lateral infra patellar region. A sleeve member 10a is inserted from the lateral region and has a meniscus clamp 111 inserted therethrough. A second sleeve member 10b is shown in a medial inferior position with a meniscotone 112 positioned through its channel. Additional sleeves 10 may be positioned in the vicinity of the joint as desired for a particular surgical procedure. The operator observes the interior portion of the joint through the arthroscope 10 while manipulating surgical tools such as the meniscus clamp 111 and meniscotome 112 to effect surgical procedures within the joint area.

It is within contemplation that a double ocular arthroscope 110 be used. A double ocular arthroscope has two viewing locations 114 on one instrument as shown for the arthroscope 110 in FIG. 15. With two viewing locations, two persons may jointly perform the surgical procedures. For example, one person may manipulate the arthroscope and retract the meniscus using instruments inserted through the sleeve 10a. The other person (e.g., surgeon) may view the retracted minuscus and concentrate on excising the minuscus using instruments positioned through one or more sleeves 10b.

The instruments 111 and 112 are sized in cross-section slightly less than the cross-section of the channel 18 of the sleeve 10 to permit slideable movement therethrough while minimizing leakage of the pressurized fluid in the articulate joint area. The sleeve 10 flexes and elastically distends as the instruments 111 and 112 are manipulated. The lip 37 of the sleeve 10 provides a substantially tight flexible seal about the instruments 111 and 112 to further reduce leakage of the fluid.

Surgical conditions or procedures which may be effected include meniscectomy, anterior and posterior cruciate ligament repair, chondromalcia of the patella and of the femoral condyle, osteochondritis dissecans, osteochondral fracture, fracture of the tibial spines, fractures of the femoral condyle, removal of loose bodies, removal of foreign bodies, and the like. Indeed, almost the full gamut of knee surgery may be effected using the procedure and the instrumentation described.

The system of surgery and the apparatus herein described permits major surgery to be effected using small stab wounds about the knee or other articulate joint. As opposed to the arthrotomy incisions of two to three inches used in conventional surgery, the trauma imparted to the patient is markedly reduced. Accordingly, after surgery the patient should be able to leave the hospital on the same day or shortly thereafter. Little or no time on crutches wll be necessary. Further, no supervised physical therapy should be required because of the minimized damage to tissue and muscle. Aside from the relief of pain and suffering, as well as relief from extended disability, the economics of knee surgery should be significantly reduced. Dollar savings should be realized on medical bills from the reduced amount of hospitalization, the reduced amount of surgical time, and the reduced amount of therapeutic time associated with many forms of arthrotomic surgery for which the procedure and apparatus herein disclosed may be used.

It is to be understood that the embodiments of the invention herein described are merely illustrative of the application of the principals of the invention. Reference herein to details of the illustrated embodiments and procedures is not intended to limit the scope of the claims which themselves recite those features regarded as essential to the invention.

I claim:

1. A surgical method comprising:
   positioning a preselected quantity of distortable sleeves having a channel to extend from the anterior surface of the patient through the synovial layer of an articulate joint of a patient;
   positioning a viewing apparatus through the said synovial layer; and
   inserting surgical instruments through said sleeves and manipulating said instruments to effect therapeutic and surgical procedures within the joint area while viewing through said viewing apparatus .

2. The method of claim 1 wherein said sleeve devices are positioned using: (1) a first inserter having a collar which abuts the anterior end of said sleeve and a blade which extends through and beyond the interior end of said sleeve; and (2) a second inserter having a collar which abuts the anterior end of said sleve and a blunt member which extends through and beyond the interior end of said sleeve, whereby said first inserter is operated to carry the interior end of said sleeve through the skin, subcutaneous tissue and fascia and thereafter said first inserter is replaced with said second inserter and said second inserter is operated to carry said interior end of said sleeve through said synovial layer.

3. The method of claim 2 wherein a wire is inserted through an aperture in said second inserter to extend beyond the interior end of said sleeve to remain in position upon removal of said second inserter and sleeve to localize the treatment stab wound for subsequent reinsertion of said sleeve.

4. The method of claim 1 wherein said viewing apparatus is an arthroscope.

5. The method of claim 1 wherein said viewing apparatus is a double ocular arthroscope wherein a first operator views through a first viewing location and manipulates surgical instruments positioned through at least one sleeve and a second operator views through a second viewing location and manipulates surgical instruments positioned through at least one sleeve in cooperation with said first operator.

6. The method of claim 1 wherein said articulate joint is pressurized with fluid, wherein said sleeve channel is removably and anteriorly capped to retain said pressure, and wherein said surgical instruments are sized in cross-section substantially to the cross-section of said channel to be essentially liquid tight and slideably movable through said channel are promptly positioned in said channel, and upon uncapping.

* * * * *